US006476291B1

(12) United States Patent
Conner

(10) Patent No.: US 6,476,291 B1
(45) Date of Patent: *Nov. 5, 2002

(54) TRUE BREEDING TRANSGENICS FROM PLANTS HETEROZYGOUS FOR TRANSGENE INSERTIONS

(75) Inventor: Anthony John Conner, Christchurch (NZ)

(73) Assignee: New Zealand Institute for Food and Crop Research Limited, Canterbury (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 09/520,366

(22) Filed: Mar. 7, 2000

Related U.S. Application Data

(60) Division of application No. 09/100,879, filed on Jun. 22, 1998, now Pat. No. 6,057,496, which is a continuation-in-part of application No. PCT/NZ96/00148, filed on Dec. 20, 1996.

(51) Int. Cl.[7] .................. C12N 15/82; C12N 15/90; C12N 5/04; A01H 1/00; A01H 5/10
(52) U.S. Cl. .................. 800/278; 435/419; 435/468; 800/260; 800/298; 800/300; 800/306; 800/323
(58) Field of Search .................. 435/69.1, 418, 435/419, 468; 800/260, 278, 298, 300, 306, 323, 320, 290, 295

(56) References Cited

U.S. PATENT DOCUMENTS

| 5,254,801 A | 10/1993 | Dotson et al. .............. 800/278 |
| 5,278,057 A | 1/1994 | Jorgensen .................. 435/468 |
| 5,426,041 A | 6/1995 | Fabijanski et al. .......... 435/468 |
| 5,633,441 A | 5/1997 | De Greef et al. ........... 800/278 |
| 5,652,354 A | 7/1997 | Mariana et al. ............ 536/24.1 |

OTHER PUBLICATIONS

Watson et al., *Molecular Biology of the Gene*, 4th ed., 1992, 2 title pages and pp. 727–729.

Conner and Christey, *Biocontrol Science and Technology*, 4:463–473 (1994).

Bayley et al., "Engineering 2,4–D Resistance Into Cotton," *Theor Appl Genet*, 83:645–649 (1992).

Conner et al., "Brassica Napus Mutants With Increased Chlorsulfuron Resistance," *Proc. 47th New Zealand Plant Protection Conf.*, 173–177 (1994).

Guerineau et al., "Sulfonamide Resistance Gene for Plant Transformation," *Plant Molecular Biology*, 15:127–136 (1990).

McKersie, B.D. and S.R. Bowley, "Somatic Embryogenesis: Forage Improvement using Synthetic Seeds and Plant Transfromation," In Molecular and Cellular Technologies for Forage Improvement, Proceedings of a symposium sponsored by Divisions C–1, C–6, and C–7 of the Crop Science Society of America in Indianapolis, IN, Nov. 6, 1996, E.C. Brummer et al. (editors). *CSSA Special Publication* No. 26:117–134 (1998).

Potrykus, *Ann. Rev. Plant Physiol. Mol. Biol.*, vol. 42, pp. 205–225 (1991).

Lyon et al., *Plant Mol. Bio*, vol. 13, pp. 533–540 (1989).

Li et al., *Plant Physiol*, vol. 100, pp. 662–668 (1992).

D'Ovidio, *Plant Mol. Biol.* vol. 22, pp. 1173–1176 (1993).

*Hybridization of Crop Plants*, pp. 317, 513 and 659 (1980), Fehr, W.R. and Hadley, H. H., Eds.

*Primary Examiner*—Amy J. Nelson
*Assistant Examiner*—Ashwin Mehta
(74) *Attorney, Agent, or Firm*—Morgan, Lewis & Bockius

(57) ABSTRACT

The invention provides a method for biasing a crop plant which is heterozygous for a transgene towards the production of seeds which carry the transgene comprising the step of contacting the crop plant containing a gene construct comprising the transgene coding for resistance to a specific phytotoxin with the specific phytotoxin one or more times during the life of the crop plant. The method achieves this through selective inhibition of phytotoxin-sensitive plant ovules, embryos and pollen. The method has particular application to the production of open pollinated and synthetic varieties of crop plants, such as alfalfa synthetic varieties.

24 Claims, No Drawings

TRUE BREEDING TRANSGENICS FROM PLANTS HETEROZYGOUS FOR TRANSGENE INSERTIONS

CROSS REFERENCE TO RELATED APPLICATIONS

This application is a divisional of application Ser. No. 09/100,879, filed Jun. 22, 1998 (now U.S. Pat. No. 6,057, 496), which is a continuation-in-part of PCT/NZ96/00148, filed on Dec. 20, 1996, which claims priority to New Zealand Patent Application No. 280742, filed on Dec. 21, 1995, both applications which are hereby incorporated by reference in their entirety.

FIELD OF THE INVENTION

The present invention pertains, in general, to methods for producing transgenic seeds. In particular, it relates to methods for ensuring that crop plants which are heterozygous for the presence of a transgene produce seeds which always carry the transgene.

BACKGROUND OF THE INVENTION

All publications and patent applications herein are incorporated by reference to the same extent as if each individual publication or patent application was specifically and individually indicated to be incorporated by reference.

A major problem associated for the commercialization of transgenic cultivars in highly heterozygous crops is the segregation of transgenes during seed production (Conner and Christey *Biocontrol Science and Technology* 4:463–473 (1994)). In order to develop a cultivar involving crosses between heterozygous individuals (e.g.: asparagus, forage brassicas, pasture species, forest trees, etc.), it will be necessary to intermate individuals heterozygous for transgenes. In many open pollinated or synthetic cultivars this will usually involve the intermating of several transgenic lines independently derived for different individual plants. This will involve the parents of synthetic cultivars, or a sufficient number of different individuals to maintain an effective population size to avoid inbreeding depression/ genetic drift within the population. The transgenic individuals utilized in producing transgenic synthetic populations may arise from single event transformations of a single plant. When this is the case, the transgene could be introduced into a synthetic population, such as an alfalfa synthetic population, by making multiple crosses of the individual transgenic alfalfa plant with a number of different non-transgenic alfalfa plants from one or more alfalfa lines. Alternatively, since the transgenic individuals to be intermated may be derived from independently derived transformed plants, the is transgenes may be located at different loci. The resulting intermated progeny will therefore be segregating at all the loci and the transgenic traits will have a "quantitative basis" (Conner and Christey, supra). As discussed immediately below, the prior art has failed to address the segregation and consequent loss of transgenes in open pollinated and synthetic populations.

U.S. Pat. No. 5,254,801 discloses methods whereby plant cells and whole plants can be genetically modified so as to selectively induce cellular lethality using heterologous dominant, conditionally lethal genes in combination with selected protoxin compounds. The methods are for inducing male sterility for the hybrid seed production, including alfalfa, canola, and oil seed rape. This patent fails to disclose a method of producing heterologous plants which utilizes a transgene coding for resistance to a specific phytotoxin.

U.S. Pat. No. 5,278,057 describes a method of producing plants with a marker closely linked to a target locus, in particular a nuclear male sterile target locus. The method involves transformation of a group of plants in order to introduce a marker into each plant, and isolation of a plant with the marker closely linked to a target locus. The markers include visible markers and dominant conditional lethal markers (e.g., antibiotic resistance or herbicide resistance). The method is of particular use for hybrid seed production of any crop plant where the target locus is a nuclear male sterile locus, including rapeseed, alfalfa, clover, cole crops or *Brassica oleracea*.

U.S. Pat. No. 5,426,041 discloses a method for seed preparation which comprises:
a) crossing a male sterile plant and a second plant which is male fertile,
b) obtaining seed of said male sterile plant, wherein the seed has integrated into its genome:
1) a first recombinant DNA molecule having a first DNA sequence which encodes a first gene product and a first promoter which is capable of regulating the expression of said first DNA sequence; and,
2) a second recombinant DNA molecule which contains a second DNA sequence which encodes a second gene product and a second promoter which is capable of regulating the expression of said second DNA sequence.

The first and second gene products cooperate to selectively interfere with the function and/or development of cells of a plant that are critical to pollen formation and/or function of a plant grown from said seed, such that any plant grown from the seed is substantially male sterile.

More specifically, the '041 patent further teaches a procedure to produce hybrid seed which includes using an IamS/IamH genetic system. The procedure can include linking the IamH gene to a gene for herbicide resistance so that the herbicide can be used for the roguing of the plant line A1; and, that herbicide application takes place after flowering and will kill the A1 so that only seed that has the genotype A1/A2 is produced. The A1/A2 seed is substantially 100% male sterile and can be pollinated with a male fertile line leading to commercial hybrid seed.

U.S. Pat. No. 5,633,441 is directed to plants comprising female-sterility-DNA encoding a protein or polypeptide such as barnase which, when produced in the cells of the plant, kills or significantly disturbs the metabolism, functioning or development of the cells. The foreign DNA also comprises a first promoter which directs expression of the female-sterility DNA selectively in style cells, stigma cells or style and stigma cells of the female reproductive organs of the plants. The first promoter does not direct detectable expression of the female sterility DNA in the ovule or in other parts of the plant so that the plant remains male-fertile. The female-sterility DNA is in the same transcriptional unit as and under the control of the first promoter. More specifically, the '441 patent discloses a foreign chimaeric DNA sequence that comprises the female-sterility DNA and a first promoter and that can also comprise a marker DNA and a second promoter. Preferred markers include herbicide tolerance or resistance genes.

The '441 patent further discloses a process for producing hybrid seeds, which grow into hybrid plants, by crossing: 1) the female-sterile plant of this invention which may include, in its nuclear genome, the marker DNA, preferably encoding a protein conferring a resistance to a herbicide on the plant; and 2) a female-fertile plant without the marker DNA in its genome.

U.S. Pat. No. 5,652,354 relates to promoters from endogenous genes of plants, is wherein said promoters direct gene expression selectively in stamen cells of said plant, particularly in tapetum cells of said plant. The promoters may be used to transform a plant with a foreign DNA sequence encoding a product which selectively disrupts the metabolism, functioning, and/or development of stamen cells of the plant. The male-sterility DNA and its associated promoter are exemplified as being foreign DNA sequences. Preferred marker DNAs are those which inhibit or neutralize the action of herbicides.

None of these patents discloses a method of producing an open-pollinated population or synthetic variety whereby a transgene is maintained at sufficiently useful levels during subsequent generations of inter- and intra-crossing of the parental lines which made up the original population or variety.

It would be highly desirable to have a method to prevent the formation of, or eliminate, the individual seeds that do not carry a transgene. If this could be achieved, all the seeds in subsequent generations would carry a transgene, without interfering with the highly heterozygous genetic background of the cultivar. It would also offer a more convenient strategy for introgression of transgenes into open pollinated crop cultivars. A single transgenic individual could be intermated to many other individuals, with the high proportion of non-transgenic progeny being prevented from developing in seed production blocks prior to or during flowering and seed development.

Thus, the object of this invention to provide methods for producing segregating populations in which one or more transgenes are maintained in a large enough percentage of the plants so that the beneficial effect of the transgenes are realized.

SUMMARY OF THE INVENTION

In one aspect, the present invention can be said to broadly consist in a method for biasing a crop plant which is heterozygous for a transgene towards the production of seeds which carry the transgene comprising the step of contacting a crop plant containing a gene construct comprising a transgene coding for resistance to a specific phytotoxin with said specific phytotoxin one or more times during the life of said plant.

In still another aspect the invention provides a method of selectively inhibiting phytotoxin-sensitive plant ovules, embryos and/or pollen in order to bias a crop plant which is heterozygous for a transgene towards the production of seeds which carry the transgene comprising the step of contacting a crop plant containing a gene construct comprising a transgene coding for resistance to a specific phytotoxin with said specific phytotoxin one or more times during the life of said plant.

In yet another aspect, the invention provides a method of selectively inhibiting phytotoxin-sensitive plant ovules in order to bias a crop plant which is heterozygous for a transgene towards the production of seeds which carry the transgene comprising the step of contacting a crop plant containing a gene construct comprising a transgene coding for resistance to a specific phytotoxin with said specific phytotoxin one or more times during the life of said plant.

In a further aspect, the invention provides a method of selectively aborting phytotoxin-sensitive plant embryos in order to bias a crop plant which is heterozygous for a transgene towards the production of seeds which carry the transgene comprising the step of contacting a gene construct comprising a transgene coding for resistance to a specific phytotoxin with said specific phytotoxin one or more times during the life of said plant.

In yet a further aspect, the invention provides a method of selectively inhibiting phytotoxin-sensitive pollen in order to bias a crop plant which is heterozygous for a transgene towards the production of seeds which carry the transgene comprising the step of contacting a crop plant containing a gene construct comprising a transgene coding for resistance to a specific phytotoxin with said specific phytotoxin one or more times during the life of said plant.

In addition to the phytotoxin resistance gene, the gene construct may also contain additional liked transgene(s) which are co-transferred to the transgenic plant.

Conveniently, the method includes the preliminary step of introducing said gene construct into said plant or into the seed from which said plant is grown.

In preferred embodiments, the method includes the subsequent step of collecting the seed produced by the plant, and confirming the presence of the gene construct.

The phytotoxin which is applied to the plant can be an antibiotic or a herbicide. It is however presently preferred that the phytotoxin be a herbicide. It is further preferred that the herbicide be one which translocates throughout the plant upon application.

In a further embodiment, the invention provides seeds carrying a gene construct produced by the method defined above.

Although the present invention is broadly as defined above, it will be appreciated by those person skilled in the art that it is not limited thereto and that it further includes the embodiments which are described below.

Further objects and advantages of the present invention will be clear from the description that follows.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

It will be appreciated from the above that the method of the invention has application to all crops where seed is produced from heterozygous plants. Such crop plants include forage crops such as forage brassica, forage legumes and grasses, trees, vegetables and ornamental flowers.

Overview of the Invention

The critical step of the method is the application of a phytotoxin to the crop plant during its life. Usually, the phytotoxin will be applied during the vegetative or reproductive growth phase of the plant. The plant to which the phytotoxin is applied will be one which has either been directly transformed by introduction of a gene construct (comprising a gene coding for resistance to the phytotoxin and, optionally, one or more closely linked additional genes) or one which has been grown from seed which itself carries the gene construct.

It is contemplated that the phytotoxin be applied to the plant only once during its life. However, in preferred embodiments, the phytotoxin will be applied more than once, and most preferably two or three during the vegetative or reproductive growth phase.

As indicated above, the gene construct can be two components. The first component, which will always be present, is a gene coding for resistance against a phytotoxin. The phytotoxin resistance component of the gene construct can code for genes conferring resistance to antibiotics or similar chemicals e.g. kanamycin resistance (Bevan et al. *Nature* 304: 184–187 (1983); Fraley et al., *Proceedings of the National Academy of Sciences USA* 80: 4803–4807 (1983); Herrera-Estrella et al., *The EMBO Journal* 2: 987–995 (1983); De Block et al., *The EMBO Journal*, 3; 1681–1689 (1984); Horsch et al., *Science*, 223: 469–498 (1984); Horsch et al., *Science*, 227: 1229–1231 (1985)), methotrexate resistance (Herrera-Estrella et al., *The EMBO Journal* 2: 987–955 (1983)), chloramphenicol resistance De Block et al., *The EMBO Journal*, 3: 1681–1689 (1984)), hygromycin resistance (Walden et al., *Plant Molecular Biology* 5: 103–108 (1985); van der Elzen et al., *Plant Molecular Biology* 5: 299–302), bleomycin resistance (Hille et al., *Plant Molecular Biology* 7: 171–176 (1986), streptomycin resistance (Jones et al., *Molecular and General Genetics* 210: 86–91 (1987)), phleomycin resistance (Perez et al., *Plant Molecular Biology* 13: 365–373), sulfonamide resistance (Guerineau et al., *Plant Molecular Biology* 15: 127–136 (1990)), S-aminoethyl L-cysteine resistance (Perl et al., *Bio Technology* 11: 715–718 (1993), and genetamycin resistance (Hayford et al., *Plant Physiology* 86: 1216–1222 (1988); Gossele et al., Plant Molecular Biology 26: 2009–2012 (1994)).

It is however preferred that it be a coding for herbicide resistance, such as glyphosate resistance (Comai et al., *Nature* 317: 741–744 (1985)), phosphinothricin resistance (De Block et al., *The EMBO Journal* 6: 2513–2518 (1987); Wohllenben et al., *Gene* 70: 25–37 (1988)), atrazine resistance (Cheung et al., *Proceedings of the National Academy of Sciences USA* 85: 391–395 (1988)); sulfonylurea resistance (Haughn et al., *Molecular and General Genetics* 210: 266–271 (1988); Lee et al., *The EMBO Journal*, 7: 1241–1248 (1988)), bromoxynil resistance (Stalker et al., *Science* 242: 419–423 (1988)), 2,4-D resistance (Steber and Willmitzer Bio/Technology 7: 811–816 (1989); Lyon et al., *Plant Molecular Biology* 13: 533–540 (1989); Bayley et al, *Theoretical and Applied Genetics* 83: 645–649 (1992)), cyanamide resistance (Maier-Greniner et al., *Angewandte Chemie, International Edition in English* 30: 1314–1315 (1991)), and dalapon resistance (Buchanan-Wollaston et al., *Plant Cell Reports* 11: 627–631 (1992)).

It is especially preferred that this component of the construct code for resistance against a herbicide which is capable of translocating throughout the plant to which it is applied. Examples of such herbicides are chlosulfuron and N-phosphonomethylglycine (glyphosate).

The second, and optional, component of the gene construct is at least one additional gene directly or closely linked to the phytotoxin resistance gene. This gene can be any transgene (i.e. a gene from another plant or organism or a synthetic gene) desirable for introduction into the particular crop plant. Examples of such transgenes include resistance to pests and diseases e.g. insect-resistance cotton and corn (Perlak et al., *Bio/Technology* 8: 939–943 (1990); Koziel et al., Bio/Techhnology 11: 194–200)), virus-resistant alfalfa (Hill et al., *Bio/Techhnology* 9: 373–377 (1991)) and fungal-resistant rapeseed (Broglie et al., *Science* 254: 1194–1197 (1991)) or improved quality traits such as improved protein content in alfalfa (Schroeder et al., *Australian Journal of Plant Physiology* 18: 495–505 (1991) and modified oils in rapeseed (Knutson et al., *Proceedings of the National Academy of Sciences USA* 89: 2624–2628 (1992)). Alternatively the second component may not be a transgene but instead be an existing gene within the chromosomes of the plant which it is desirable to introduce an extra copy of.

The construct can be introduced into the plant or seed using any suitable procedure known in the art. Examples of such procedures include Agrobacterium-mediated transformation, direct DNA transfer to plant protoplasts or intact plant tissues using techniques such as electroporation, chemical-induced uptake, or microprojectile bombardment, or any of the range of other methods that are reported to accomplish gene transfer (seer reviews by Gasser and Fraley, *Science* 244: 1293–1299 (1989); Potrykus, *Annual Review of plant Physiology and Plant Molecular Biology* 42: 205–225 (1991); Klein et al., *Bio/Techhnology* 10: 286–291 (1992) and citations within these reviews).

It will be appreciated that when the gene construct includes the phytotoxin resistance gene only, it can nevertheless be linked to a gene of the plant which it would be desirable to ensure is always present in the seed obtained from the plant. This can be achieved by introducing the gene construct containing the phytotoxin resistance gene into the plant at an integration site very close to the site of the gene in question.

The seed which carries the gene construct is of course the commercial focus of the invention. The presence of the construct can be determined directly in the seed itself using methods routinely available in this art (for example using nucleic acid hybridization protocols) or can be demonstrated in the plant which is grown from the seed.

Definitions

As used herein, the term "alfalfa" means any Medicago species, including, but not limited to, *M. sativa, M. murex, M. falcata*, and *M. prostrata*. Thus, as used herein, the term "alfalfa" means any type of alfalfa including, but is not limited to, any alfalfa commonly referred to as cultivated alfalfa, diploid alfalfa, glanded alfalfa, purple-flowered alfalfa, sickle alfalfa, variegated alfalfa, wild alfalfa, or yellow-flowered alfalfa.

As used herein, the term "allele" means any of several alternative forms of a gene.

As used herein, the term "clover" means means any Trifolium species, including, but not limited to, *T. hybridum, T. vesiculosum, T. alexandrinum, T. incarnatum, T. campestre, T. dubium, T. ambiguum, T. arvense, T. pratense, T. fragiferum, T. subterraneum, T. repens*, and *T. medium*. Thus, as used herein, the term "clover" means any type of clover including, but is not limited to, any clover commonly referred to as alsike clover, arrowleaf clover, berseem clover, crimson clover, large hop clover, small hop clover, Kura clover, rabbit's foot clover, red clover, strawberry clover, subterranean clover, white clover, and zigzag clover.

As used herein, the term "crop plant" means any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food additives, smoking products, pulp production and wood production.

As used herein, the term "cross pollination" or "cross-breeding" means the pollen of one flower on one plant is applied (artificially or naturally) to the ovule (stigma) of a flower on another plant.

As used herein, the term "cultivar" means a variety, strain or race of plant which has been produced by horticultural or agronomic techniques and is not normally found in wild populations.

As used herein, the term "genotype" means the genetic makeup of an individual cell, cell culture, plant, or group of plants.

As used herein, the term "heterozygote" means a diploid or polyploid individual cell or plant having different alleles (forms of a given gene) at least at one locus.

As used herein, the term "heterozygous" means the presence of different alleles (forms of a given gene) at a particular gene locus.

As used herein, the term "homozygote" means an individual cell or plant having the same alleles at one or more loci.

As used herein, the term "homozygous" means the presence of identical alleles at one or more loci in homologous chromosomal segments.

As used herein, the term "hybrid" means any individual plant resulting from a cross between parents that differ in one or more genes.

As used herein, the term "inbred" or "inbred line" means a relatively true-breeding strain.

As used herein, the term "locus" (plural: "loci") means any site that has been defined genetically. A locus may be a gene, or part of a gene, or a DNA sequence that has some regulatory role, and may be occupied by different sequences.

As used herein, the term "mass selection" means a form of selection in which individual plants are selected and the next generation propagated from the aggregate of their seeds.

As used herein, the term "open pollination" means a plant population that is freely exposed to some gene flow, as opposed to a closed one in which there is an effective barrier to gene flow.

As used herein, the terms "open-pollinated population" or "open-pollinated variety" mean plants normally capable of at least some cross-fertilization, selected to a standard, that may show variation but that also have one or more genotypic or phenotypic characteristics by which the population or the variety can be differentiated from others. A hybrid which has no barriers to cross-pollination is an open-pollinated population or an open-pollinated variety.

As used herein, the term "ovule" means the female gametophyte, whereas the term "pollen" means the male gametophyte.

As used herein, the term "phenotype" means the observable characters of an individual cell, cell culture, plant, or group of plants which results from the interaction between that individual's genetic makeup (i.e., genotype) and the environment.

As used herein, the term "self-incompatible" means the failure, following mating or pollination, of a male gamete and a female gamete to achieve fertilization, where each of them is capable of uniting with other gametes of the breeding group after similar mating or pollination (Mather, *J. Genet.* 25:215–235 (1943)).

As used herein, the term "self pollinated" or "self-pollination" means the pollen of one flower on one plant is applied (artificially or naturally) to the ovule (stigma) of the same or a different flower on the same plant.

As used herein, the term "synthetic" means a set of progenies derived by intercrossing a specific set of clones or seed-propagated lines. A synthetic may contain mixtures of seed resulting from cross-, self-, and sib-fertilization.

As used herein, the term "transformation" means the transfer of nucleic acid (i.e., a nucleotide polymer) into a cell. As used herein, the term "genetic transformation" means the transfer and incorporation of DNA, especially recombinant DNA, into a cell.

As used herein, the term "transgenic" means cells, cell cultures, plants, and progeny of plants which have received a foreign or modified gene by one of the various methods of transformation, wherein the foreign or modified gene is from the same or different species than the species of the plant receiving the foreign or modified gene.

As used herein, the term "variety" means a subdivision of a species, consisting of a group of individuals within the species which are distinct in form or function from other similar arrays of individuals.

Specific Crop Examples

1. Alfalfa

Alfalfa (*Medicago sativa L.*) is an important forage species for hay and pasture which has been referred to as the "Queen of the Forages" because of its high yields and feeding value. Alfalfa is recognized as the most widely adapted agronomic crop, as an effective source of biological nitrogen ($N_2$) fixation, useful in the improvement of soil tilth, as an important source of protein yield/ha, and as an attractive source of nectar for honey bees. For a comprehensive review of the benefits of alfalfa as an agronomic crop, see Barnes et al., *Highlights in the USA and Canada* 1:2–24, In *Alfalfa and Alfalfa Improvement*, Hanson et al. (ed.), American Society of Agronomy, Monograph No. 29 (1988).

Although alfalfa originated in southwestern Asia, it is well adapted to a wide range of climates and soils in the United States, where about 11 million ha are grown annually. Between 1900 and 1975 more than 160 cultivars were developed for production in North America. Most of the newer cultivars were selected for improved adaptation and multiple pest resistance. For a comprehensive review of the distribution, history and origin of alfalfa, see Michaud et al, *World Distribution and Historical Development* 2:25–91, In *Alfalfa and Alfalfa Improvement*, supra; and, Quiros et al., *The Genus Medicago and the Origin of the Medicago sativa Complex* 3:93–124, In *Alfalfa and Alfalfa Improvement*, supra.

The genus Medicago is widely distributed and comprises an array of diverse species that are either annual or perennial. The most recent taxonomic studies of the perennial species concluded that *M. sativa* is polymorphic. Lesins and Gillies (Taxonomy and cytogenetics of *Medicago* 353–386, In *Alfalfa science and technology*, C. H. Hanson (ed.), American Society of Agronomy, (1972)) defined the complex as *M. sativa-falcata-glutinosa*, and Gunn et al. (*USDA Tech. Bull. No.* 1574 (1978)) designated it as the *M. sativa sensu lato* complex.

*M. sativa* plants are autopolyploid organisms, or more specifically, autotetraploids. More specifically, *M. sativa* plants are polysomic polyploid organisms which display tetrasomic inheritance patterns.

Essentially all annual species are cleistogamous and are exclusively self-pollinated. Generally, the perennial species require tripping, as by insect visits to the floral structures, and will set seed from either self or cross-pollination. Crosses can be made among subspecies in the *M. sativa* complexes and between the cultivated tetraploids and wild diploids without special preparation of the parents. For a comprehensive review of the floral characteristics, plant culture, and methods of self-pollinating or hybridizing alfalfa, see D. K. Barnes, *Alfalfa* 9:177–187, In *Hybridization of Crop Plants*, Fehr et al. (ed.), American Society of Agronomy Inc. (1980).

Commercial alfalfa seed may be provided either in a synthetic variety or a hybrid variety. Commercial production of synthetic varieties may include a breeder seed production stage, a foundation seed production stage, a register seed production stage and a certified seed production stage. Hybrid variety seed production may involve up to three stages including a breeder seed production stage, a foundation seed production stage and a certified seed production stage.

Breeder seed is an initial increase of seed produced from the strains or clones that are developed by a breeder. Foundation seed is a second generation increase of seed produced from the breeder seed. Register seed may be derived from foundation seed. Certified seed may be derived from breeder seed, foundation seed or register seed. Breeder seed descends from a selection of recorded origin, under the direct control of the breeder, a delegated representative or a state or federal inspection service, such as the AOSCA (Association of Official Seed Certification Analysts) in the U.S.A. Certified seed is used in commercial crop production. Certified seed is usually grown, processed and labeled under supervision and regulation of a public agency.

Efforts in developing healthy and productive alfalfa varieties often focus on breeding for disease and stress-resistant cultivars, for example, breeding for persistence, breeding for adaptation to specific environments, breeding for yield per se, and breeding for quality. Success has been attained in breeding for resistance to fungal, bacterial, insect, and nematode pests, including, but not limited to the development of varieties tolerant/resistant to bacterial wilt and common leaf spot (see, e.g., Elgin, Jr., et al., *Breeding for Disease and Nematode Resistance* 827–858, In Alfalfa and Alfalfa Improvement, supra) and to the spotted alfalfa aphid and alfalfa weevil (see, e.g., Sorensen et al., *Breeding for Insect Resistance* 859–902, In Alfalfa and Alfalfa Improvement, supra). Breeders have had less success in breeding for yield and quality per se (see, e.g. Hill et al., *Breeding for Yield and Quality* 26:809–825, In Alfalfa and Alfalfa Improvement, supra), although methods have been developed that help increase productivity and yield (U.S. Pat. No. 4,045,912). Historically, yield and productivity, quality and persistence are objectives of high concern to farmers.

2. Clover

The clover species described herein are the true clovers belonging to the genus Trifolium. The species of major agricultural importance in the Untied States are red clover (*T. pratense L.*), white clover (*T. repens L.*), crimson clover (*T. incarnatum L.*), and alsike clover (*T. hybridum L.*). Crimson clover is an annual species, and the others are perennial. These clovers are thought to have originated in Asia minor or southeastern Europe. They are grown extensively for hay, pasture, and soil improvement throughout the eastern half of the United States and under irrigation in the Pacific and adjacent states.

The genus Trifolium consists of about 240 species divided by taxonomists into about 16 sections (Hossain, *Notes R. Bot. Gard. Edinb.* 23:387–481(1961)). For the most part, gene transfer between sections by conventional hybridization methods has been difficult. About 30% of the clover species are self-incompatible and are cross-pollinated by bees, and 70% are self-pollinated. Some species (e.g., crimson clover) normally cross-pollinate, but set considerable seed upon selfing. For a comprehensive review of the floral characteristics, plant culture, and methods of self-pollinating or hybridizing clover, see N. L. Taylor, *Clovers* 16:261–272, In *Hybridization of Crop Plants*, supra.

Breeding Methods

1. Open-Pollinated Populations

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population which is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988). Detailed breeding methodologies specifically applicable to alfalfa are provided in *Alfalfa and Alfalfa Improvement*, supra.

2. Mass Selection

In mass selection, desirable individual plants are chosen, harvested, and the seed composited without progeny testing to produce the following generation. Since selection is based on the maternal parent only, and their is no control over pollination, mass selection amounts to a form of random mating with selection. As stated above, the purpose of mass selection is to increase the proportion of superior genotypes in the population.

3. Synthetics

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100–200 being the average. Broad based synthetics formed from 100 or more clones would be expected to be more stable during seed multiplication than narrow based synthetics.

Synthetics in alfalfa are used in advanced generations as commercial cultivars. The parents are always selected for some particular trait or traits but seldom for combining ability per se. Synthetic cultivars permit the expression of heterosis to a degree, usually less than hybrids, while providing a practical method for seed multiplication.

Parents for synthetic cultivars in alfalfa are selected by many different methods. In an open breeding system the parents can be selected from such diverse sources as ecotypes, cultivars, and experimental strains. Although production of a synthetic cultivar is relatively simple, a wise choice of parents for the Syn 0 generation is crucial, for this will determine the performance of the synthetic. Decisions as to which and how many parents to include, fix the minimum degree of inbreeding that the eventual cultivar will sustain in subsequent generations.

4. Hybrids

A hybrid is an individual plant resulting from a cross between parents of differing genotypes. Commercial hybrids are now used extensively in many crops, including corn (maize), sorghum, sugarbeet, sunflower and broccoli. Hybrids can be formed a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an outbreeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity which results in increased vigor of growth, survival, and fertility of hybrids as compared with the parental lines which were used to form the hybrid. Maximum heterosis is usually achieved by crossing two genetically different, highly inbred lines.

Theoretically, maximum heterozygosity and hybrid vigor in alfalfa is believed to be expressed only in a tetra-allelic condition (Bingham et al., *Maximizing heterozygosity in authopolyploids* 471–489, In *Polyploidy: Biological Relevance*, Lewis (ed.), Plenum Press (1979); Bingham et al., *Maximizing Heterozygosity in Autopolyploids* 130–143, In *Better Crops for Food*, CIBA Found. Symp. 97, Pitman Books (1983)). This could be accomplished by using four parental strains instead of the two proposed for the production of most diploid hybrid cultivars. In this way up to 75% of the plants in commercial alfalfa plantings could be double cross hybrids and thus potentially tetra-allelic. On a practical basis, hybrid alfalfa has not been commercially viable because: 1) the cost of seed production is prohibitive due to the fact that seed is harvested only from the female plants, not all of the plants in the production field; and, 2) the benefits of hybrid yield, such as increased forage yield due to hybrid vigor, have not been sufficient to offset the increased costs of producing the hybrid alfalfa seed.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161–176, In *Hybridization of Corp Plants*, supra Plant Transformation 1. Introduction To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can than be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome.

Homologous recombination and site-directed integration in plants are discussed in U.S. Pat. Nos. 5,451,513, 5,501, 967 and 5,527,695.

2. Transformation Methods

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and Agrobacterium-mediated transformation (see, e.g., U.S. Pat. Nos. 5,405,765, 5,472,869, 5,538,877, 5,538,880, 5,550,318, 5,641,664, 5,736,369 and 5,736369; Watson et al., *Recombinant DNA*, Scientific American Books (1992); Hinchee et al., *Bio/Tech*. 6:915–922 (1988); McCabe et al., *Bio/Tech*. 6:923–926 (1988); Toriyama et al., *Bio/Tech*. 6:1072–1074 (1988); Fromm et al., *Bio/Tech*. 8:833–839 (1990); Mullins et al., *Bio/Tech*. 8:833–839 (1990); and, Raineri et al., *Bio/Tech*. 8:33–38 (1990)).

Transgenic alfalfa plants have been produced by many of these methods including, but not limited to, agrobacterium-mediated transformation (Wang et al., *Australian Journal of plant Physiology* 23(3):265–270 (1996); Hoffman et al., *Molecular Plant-Microbe Interactions* 10(3):307–315 (1997); Trieu et al., *Plant Cell Reports* 16:6–11 (1996)) and particle acceleration (U.S. Pat. No. 5,324,646).

Transformation has also been successfully accomplished in clover using agrobacterium-mediated transformation (Voisey et al., *Biocontrol Science and Technology* 4(4):475–481 (1994); Quesbenberry et al., *Crop Science* 36(4):1045–1048(1996); Khan et al., *Plant Physiology* 105 (1):81–88 (1994); Voisey et al., *Plant Cell Reports* 13(6): 309–314 (1994)).

3. Transgenes

Genes successfully introduced into plants using recombinant DNA methodologies include, but are not limited to, those coding for the following traits: seed storage proteins, including modified 7S legume seed storage proteins (U.S. Pat. Nos. 5,508,468, 5,559,223 and 5,576,203); herbicide tolerance or resistance (U.S. Pat. Nos. 5,498,544 and 5,554, 798; Powell et al., *Science* 232:738–743 (1986); Kaniewski et al., *Bio/Tech*. 8:750–754 (1990); Day et al., *Proc. Natl. Acad. Sci. USA* 88:6721–6725 (1991)); phytase (U.S. Pat. No. 5,593,963); resistance to bacterial, fungal, nematode and insect pests, including resistance to the lepidoptera insects conferred by the Bt gene (U.S. Pat. Nos. 5,597,945 and 5,597,946; Hilder et al., *Nature* 330:160–163; Johnson et al., *Proc. Natl. Acad. Sci. USA*, 86:9871–9875 (1989); Perlak et al., *Bio/Tech*. 8:939–943 (1990)); lectins (U.S. Pat. No. 5,276,269); and flower color (Meyer et al., *Nature* 330:677–678 (1987); Napoli et al., *Plant Cell* 2:279–289 (1990); van der Krol et al., *Plant Cell* 2:291–299 (1990)).

Transgenic alfalfa plants have been produced using a number of different genes isolated from both alfalfa and non-alfalfa species including, but not limited to, the following: the promoter of an early nodulin gene fused to the reporter gene gusA (Bauer et al., *The Plant Journal* 10(1): 91–105 (1996); the early nodulin gene (Charon et al, *Proc. Natl. Acad. of Sci. USA* 94(16):8901–8906 (1997); Bauer et al., *Molecular Plant-Microbe Interactions* 10(1):39–49 (1997)); NADH-dependent glutamate synthase (Gantt, *The Plant Journal* 8(3):345–358 (1995)); promoter-gusA fusions for each of three lectin genes (Bauchrowitz et al., *The Plant Journal* 9(1):31–43 (1996)); the luciferase enzyme of the marine soft coral Renilla reniforms fused to the CaMV promoter (Mayerhofer et al., *The Plant Journal* 7(6): 1031–1038 (1995)); Mn-superoxide dismutase cDNA (McKersie et al., *Plant Physiology* 111(4): 1177–1181 (1996)); synthetic cryIC genes encoding a Bacillus thuringiensis delta-endotoxin (Strizhov et al., *Proc. Natl. Acad. Sci. USA* 93(26):15012–15017 (1996)); and glucanse (Dixon et al., *Gene* 179(1):61–71 (1996); Masoud et al., *Transgenic Research* 5(5):313–323)). Genes of particular interest to alfalfa breeding and production include those controlling the following traits:

1. Herbicide resistance: Roundup®, Arsenal®, and sulfonyl urea herbicides such as chlorsulfuron.
2. Insect resistance: Use of Bt or other genes conferring resistance to important insect pests such as Lygus (Lygus sp.), alfalfa caterpillar (Colias sp.), and alfalfa weevil (Hypera sp.).
3. Forage quality: Increasing rumen escape (bypass) protein, which would improve feed efficiency and utilization; decreased lignin content, which would improve digestibility and animal performance.
4. Physiological: Elimination of leaf senescence, would improve yield and quality as well as decrease leaf disease development (see, U.S. Pat. No. 5,689,042).

Genes successfully transferred into clover using recombinant DNA technologies include, but are not limited to, the following: Bt genes (Voisey et al., supra); neomycin phosphotransferase II (Quesbenberry et al., supra); the pea lectin gene (Diaz et al., *Plant Physiology* 109(4):1167–1177 (1995); Eijsden et al., *Plant Molecular Biology* 29(3): 431–439 (1995)); the auxin-responsive promoter GH3 (Larkin et al., *Transgenic Research* 5(5):325–335 (1996); seed albumin gene from sunflowers (Khan et al., *Transgenic Research* 5(3):179–185 (1996)); and genes encoding the enzymes phosphinothricin acetyl transferase, beta-glucuronidase (GUS) coding for resistance to the Basta® herbicide, neomycin phosphotransferase, and an alpha-amylase inhibitor (Khan et al., supra).

These prior art methods of producing hybrid crop plants or individual plants either eliminate/maintain certain genotypes of plants entirely by spraying a particular herbicide, or they utilize a combination of male/female sterility/fertility genes and herbicide resistance genes to select for certain genotypes.

There is currently a need for methods of maintaining as many transgenic individuals as possible in an open pollinated or synthetic population. Thus, there is currently a need for methods of concentrating a transgene in a heterozygotic population such that all of the other genes, except the transgene, are maintained in the heterozygotic condition. Such methods would allow a shifting of an open pollinated or synthetic population to one that contains a higher proportion of a desired transgene which had been introduced into such populations. In this way, as many heterozygotic individuals as possible would express the transgene in such an open pollinated or synthetic population.

The capability of the present method to bias a heterozygous phytotoxin resistant plant towards producing seeds carrying the phytotoxin resistance gene will now be exemplified by the following non-limiting experiments.

EXAMPLES

Experiment 1

Materials and Methods

A homozygous line of a Brassica napus (30b) mutant, with a single gene conferring sulfonylurea resistance (Conner et al., *Proceedings of the 47th New Zealand Plant Protection Conference*, 173–177 (1994)), was used in this study. Brassica napus are self-fertile, with about 80% of the seed normally arising from self-pollination, although a greater degree of cross-pollination may occur when insect pollinators are abundant (Downey et al., *Rapeseed and Mustard*, Chapter 35:495–509, In *Hybridization of Crop Plants*, supra). B. napus is commonly referred to as canola, rape and oilseed rape.

The 30b mutant line was hybridized to a herbicide-sensitive genotype to generate a seed population heterozygous for sulfonylurea resistance. These heterozygous seeds were sown, repotted into individual pots in a greenhouse, and individuals were randomly divided into 3 populations:

(i) plants not sprayed with the herbicide (23 plants);
(ii) plants sprayed once with chlorsulfuron (a sulfonylurea herbicide) at a rate of 3 mg/liter until runoff, just as the plants were beginning to bolt (development of flowering stems) (19 plants).
(iii) plants sprayed with chlorsulfuron at a rate of 3 mg./liter until runoff, just as the plants were beginning to bolt, and then every 2 weeks until initiation of plant senescence (18 plants).

The heterozygous plants were allowed to self pollinate and resulting seeds harvested at maturity. This next generation was screened for chlorsulfuron resistance as previously described (Conner et al (1994). Briefly, this involved surface sterilizing the seeds (10–12 minutes in 1% sodium hypochlorite, plus a drop of Tween 20), followed by 2–3 rinses in sterile water, then sowing the seeds in vitro onto the surface of a medium consisting of half strength MS salts at pH 5.8 (Murashige and Skoog *Physiologia Plantarum* 15:473–497 (1962)) supplemented with 10 μg/liter chlorsulfuron and 6.5 g/liter agar. Seeds were then germinated at 24–26° C. under cool white fluorescent lights (80–100) μmol/m2/sec; 16 h light: 8 h darkness daily).

Seeds generally germinated after 3–4 days and were scored for chlorsulfuron resistance 5–7 days after sowing. Resistant seedlings had long healthy roots (4–6 cm) that penetrated into the gelled medium, with healthy green cotyledons. Sensitive seedlings had short roots (under 1 cm long) that did not penetrate into the gelled medium, increased anthocyanin (red) pigmentation in their cotyledons and curled up margins of cotyledons.

Results

The results are given in Tables 1, 2 and 3 as follows:

TABLE 1

Segregation of herbicide resistance in plants not sprayed with chlorsulfuron.

| Plant number (wt × 30a) | Number of herbicide-resistant progeny | Number of herbicide-sensitive progeny | Chi-square for 3:1 ratio |
|---|---|---|---|
| i | 61 | 20 | 0.001 |
| ii | 46 | 16 | 0.029 |
| iii | 53 | 16 | 0.104 |
| iv | 81 | 28 | 0.040 |
| v | 48 | 23 | 2.154 |
| vi | 62 | 27 | 1.426 |
| vii | 79 | 29 | 0.228 |
| viii | 54 | 14 | 0.666 |
| ix | 67 | 14 | 2.493 |
| x | 39 | 21 | 2.678 |
| xi | 47 | 12 | 0.647 |
| xii | 53 | 19 | 0.089 |
| xiii | 93 | 30 | 0.015 |
| xiv | 80 | 21 | 0.897 |
| xv | 66 | 22 | 0.001 |
| xvi | 48 | 20 | 0.752 |
| xvii | 108 | 37 | 0.033 |
| xviii | 3 | 3 | 2.028 |
| xix | 69 | 19 | 0.506 |
| xx | 22 | 12 | 1.979 |
| xxi | 109 | 22 | 4.569 |
| xxii | 65 | 16 | 1.164 |
| xxiii | 49 | 23 | 1.931 |
| Total | 1402 | 464 | |

TABLE 2

Segregation of herbicide resistance in plants sprayed once with chlorsulfuron.

| Plant number (wt × 30a) | Number of herbicide-resistant progeny | Number of herbicide-sensitive progeny |
|---|---|---|
| i | 4 | 0 |
| ii | 125 | 0 |
| iii | 83 | 7 |
| iv | 73 | 1 |
| v | 75 | 0 |
| vi | 105 | 0 |
| vii | 125 | 0 |
| viii | 67 | 0 |
| ix | 86 | 1 |

TABLE 2-continued

Segregation of herbicide resistance in plants sprayed once with chlorsulfuron.

| Plant number (wt × 30a) | Number of herbicide-resistant progeny | Number of herbicide-sensitive progeny |
|---|---|---|
| x | 71 | 1 |
| xi | 89 | 2 |
| xii | 88 | 0 |
| xiii | 94 | 1 |
| xiv | 56 | 0 |
| xv | 80 | 1 |
| xvi | 76 | 0 |
| xvii | 145 | 2 |
| xviii | 92 | 0 |
| xix | 54 | 1 |
| Total | 1588 | 17 |

TABLE 3

Segregation of herbicide resistance in plants repeatedly sprayed with chlorsulfuron.

| Plant number (wt − 30a) | Number of herbicide-resistant progeny | Number of herbicide-sensitive progeny |
|---|---|---|
| i | 5 | 0 |
| ii | 50 | 0 |
| iii | 78 | 0 |
| iv | 50 | 0 |
| v | 48 | 0 |
| vi | 83 | 0 |
| vii | 52 | 0 |
| viii | 30 | 1 |
| ix | 20 | 0 |
| x | 10 | 0 |
| xi | 14 | 0 |
| xii | 60 | 0 |
| xiii | 17 | 0 |
| xiv | 10 | 0 |
| xv | 57 | 1 |
| xvi | 100 | 0 |
| xvii | 37 | 0 |
| xviii | 7 | 0 |
| Total | 728 | 2 |

Discussion

When heterozygous individuals of the 30b brassica mutant are allowed to self pollinate, they are expected to segregate in a 3:1 ratio for herbicide-resistant and herbicide-sensitive progeny (Conner et al., 1994). This was confirmed in this study (Table 1). However, when plants of the same genetic status were sprayed with chlorsulfuron, virtually all the progeny obtained were resistant to chlorsulfuron. This was observed for both spray regimes: plants sprayed once with chlorsulfuron at the initiation of bolting (the vegetative growth phase) (Table 2), and plants sprayed at the initiation of bolting, then subsequently every 2 weeks until maturation (Table 3).

This data clearly established that applying a herbicide (such as chlorsulfuron) to herbicide-resistant plants that are expected to produce progeny segregating for herbicide-resistant and herbicide-sensitive individuals, can prevent the development of herbicide-sensitive progeny.

Experiment 2

Materials and Methods

A further chlorsulfuron-resistant *Brassica napus* mutant (19c), of independent origin to mutant 30b (Conner et al., *Proceedings of the 47th New Zealand Plant Protection*

Conference, 173–177 (1994)) was subjected to identical experiments described above for mutant 30b.

Results

The results are given in Table 4 as follows:

TABLE 4

| Herbicide application (timing) | Number of herbicide-resistant seedlings | Number of herbicide-sensitive seedlings | Chi-square for 3:1 ratio |
|---|---|---|---|
| no spray | 366 | 140 | 1.92 (P > 0.05) |
| just prior to bolting | 398 | 31 | 72 (P < 0.001) |
| repeated fortnightly sprays from bolting | 96 | 0 | 32 (P < 0.001) |

Discussion

When the heterozygous plants were not sprayed, the selfed progeny segregated not significantly different from the expected 3:1 ratio. Following chlorsulfuron applications, highly significant skewed segregation in favor of chlorsulfuron-resistant seedlings was observed. Repeated spraying of chlorsulfuron resulted in a total absence of herbicide-sensitive progeny.

Experiment 3

Transgenic Forage Brassica Plants (Brassica Napus cv. Giant)

Materials and Methods

Plant line used: G/HR10 (Christey and Sinclair, *Plant Science*: 87 161–169 (1992)). This line contains a single insertion of the T-DNA from pKIWI110 and expresses transgenes conferring kanamycin resistance, β-glucuronidase (GUS) activity, and chlorsulfuron resistance.

Plants of the original transgenic line were cloned in vitro, then transferred to a containment greenhouse. Prior to bolting (seven weeks before the appearance of flower buds), plants were sprayed once with either water or chlorsulfuron at the equivalent rate of 20 g/ha The plants were allowed to self-pollinate and the seeds were harvested five months after spraying. The progeny germinated and histochemically screened for GUS activity.

Results

1. The progeny from plants sprayed with water segregated for GUS activity in the expected 3:1 ratio for a plant heterozygous for a single transgenic locus.
   Population A: 268 GUS-positive: 99 GUS-negative (Chi-square=0.76; 0.3>P>0.5)
   Population B: 64 GUS-positive: 24 GUS-negative (Chi-square=0.24; 0.5>P>0.7)

2. The progeny from plants sprayed with chlorsulfuron showed highly distorted segregation for GUS activity with a substantial excess of transgenic progeny over the expected 3:1 ratio.
   Population A: 78 GUS-positive: 13 GUS-negative (Chi-square=5.57; P<0.025)
   Population B: 96 GUS-positive: 16 GUS-negative (Chi-square=6.86; P<0.01)

Chi-square tests of independence on the combined data from Populations A and B revealed a highly significant difference between the frequency of GUS-positive and GUS-negative progeny from the brassica plants with and without chlorsulfuron applications (Chi-square 12:84; P<0.001).

Discussion

A single application of chlorsulfuron to brassica plants (well before flowering) is sufficient to prevent the development of many of the non-transgenic progeny expected to segregate from plants heterozygous for a single transgenic locus. It is anticipated that additional chlorsulfuron applications and/or applications later during plant development would result in complete elimination of non-tansgenic progeny.

Experiment 4

Transgenic Potato Plants (Solanum Tuberosum cv. Iwa)

Materials and Methods

The Solanum tuberosum, subspecies tuberosum, plant line used: SCI1 (Conner et al., *Journal of Cellular Biochemistry* 13D: 333 (1989)). This line of potato is transformed with the T-DNA from pKIWI100 and expresses transgenes conferring kanamycin resistance, β-glucuronidase (GUS) activity, and chlorsulfuron resistance. The cultivated varieties of potato grown in the United States and Europe are predominantly tetraploid (i.e., four complete sets of chromosomes) (Plaisted, R. L., *Potato*, Chapter 34:483–494, In *Hybridization of Crop Plants*, supra; Allard, pg. 16, supra).

Plants of the original transgenic line were vegetatively propagated via tubers which were planted in a containment greenhouse. Soon after sprouting (three weeks after planting) the plants were sprayed once with either water of chlorsulfuron at the equivalent rate of 20 g/ha Plants were self pollinated at flowering and berries harvested 15 weeks after spraying. Seeds were extracted and germinated, and the progeny histochemically screened for GUS activity.

Results

1. The progeny from plants sprayed with water clearly segregated for GUS activity. The frequencies of GUS-positive and GUS-negative progeny did not follow defined genetic ratios, however this is not unexpected in tetraploid potato, which often show distorted segregation due to the high load of recessive (sub-)lethal alleles in the genome.
   128 GUS-positive: 86 GUS-negative 2. The progeny from plants sprayed with chlorsulfuron showed highly distorted segregation of GUS activity with a substantial excess of transgenic progeny over that observed following spraying with water.
   136 GUS-positive: 12 GUS-negative Chi-square tests of independence revealed a highly significant difference between the frequency of GUS-positive and GUS-negative progeny from the potato plants with and without chlorsulfuron applications (Chi-square=45.6; P<0.001).

Discussion

A single application of chlorsulfuron to potato plants (well before flowering) is sufficient to prevent the development of many of the non-transgenic progeny expected to segregate from plants heterozygous for a single transgenic locus. It is anticipated that additional chlorsulfuron applications and/or applications later during plant development would result in complete elimination of non-transgenic progeny.

Experiment 5

Additional Crosses with Brassica Napus (30b) Mutant

Materials and Methods

To further explore the underlying reasons accounting for the induced skewed segregation, additional crosses using the 30b mutant were performed. At specified times the plants were sprayed with chlorsulfuron and the progeny evaluated as described in Experiment 1 above.

Part (a). Plants heterozygous for the chlorsulfuron-resistant mutation (wtx30b) were either not sprayed, or sprayed with chlorsulfuron at varying times during development. The self-pollinated seed was harvested, and the germinated seedlings were screened for chlorsulfuron resistance.

Results

The results are given in Table 5 as follows:

TABLE 5

| Herbicide application (timing) | Number of seeds per pod | Number of herbicide-resistant seedlings | Number of herbicide-sensitive seedlings | Chi-square for 3:1 ratio |
| --- | --- | --- | --- | --- |
| no spray | 7.2 | 148 | 59 | 1.35 ($P > 0.05$) |
| seedlings (2–3 leaves) | 5.6 | 440 | 11 | 122 ($P < 0.001$) |
| just prior to bolting | 5.4 | 565 | 5 | 177 ($P < 0.001$) |
| pods reaching full size | 5.8 | 160 | 16 | 25 ($P < 0.001$) |
| 2 weeks after pods full size | 6.2 | 184 | 26 | 18 ($P < 0.001$) |

Discussion

When the heterozygous plants were not sprayed, the selfed progeny segregated not significantly different from the expected 3:1 ratio. Following chlorsulfuron applications, highly significant skewed segregation in favor of chlorsulfuron-resistant seedlings was observed. Herbicide applications from early seedlings stages to well after pods reached full size were effective at skewing segregation. The reduction in seed number per pod is suggestive that a major effect is via the elimination of herbicide-sensitive ovules or the abortion of herbicide-sensitive embryos. The skewed segregation following chlorsulfuron applications when pods have reached full size is clearly indicative of an effect on embryo abortion.

Part (b). Plants heterozygous for the chlorsulfuron-resistant mutation (wtx30b) were either not sprayed, or sprayed with chlorsulfuron at varying times during development. The back crossed-progeny ((wtx30b)xwt), resulting from pollen from non-sprayed wildtype plants were screened for chlorsulfuron resistance as described in Experiment 1.

Results

The results are given in Table 6 as follows:

TABLE 6

| Herbicide application (timing) | Number of seeds per pod | Number of herbicide-resistant seedlings | Number of herbicide-sensitive seedlings | Chi-square for 1:1 ratio |
| --- | --- | --- | --- | --- |
| no spray | 6.4 | 118 | 103 | 1.02 ($P > 0.05$) |
| just prior to bolting | 3.4 | 134 | 5 | 120 ($P < 0.001$) |
| pods reaching full size | 4.0 | 127 | 28 | 63 ($P < 0.001$) |
| 2 weeks after pods full size | 4.3 | 104 | 37 | 32 ($P < 0.001$) |

Discussion

When the heterozygous plants were not sprayed, the back-crossed progeny segregated not significantly different from the expected 1:1 ratio. Following chlorsulfuron applications, highly significant skewed segregation in favor of chlorsulfuron-resistant seedlings was observed. As in (a) above, the reduction in seed number per pod is suggestive that a major effect is via the elimination of herbicide-sensitive ovules or the abortion of herbicide-sensitive embryos. The skewed segregation following chlorsulfuron applications when pods have reached full size is clearly indicative of an effect on embryo abortion.

Part (c). Plants heterozygous for the chlorsulfuron-resistant mutation (wtx30b) were either not sprayed, or sprayed with chlorsulfuron just prior to bolting. The pollen from these plants was back-crossed to non-sprayed wildtype plants, and the resulting progeny (wtx(wtx30b)) were screened for chlorsulfuron resistance as described in Experiment 1.

Results

The results are given in Table 7 as follows:

TABLE 7

| Herbicide application (timing) | Number of seeds per pod | Number of herbicide-resistant seedlings | Number of herbicide-sensitive seedlings | Chi-square for 1:1 ratio |
| --- | --- | --- | --- | --- |
| no spray | 6.2 | 92 | 106 | 0.99 ($P > 0.05$) |
| just prior to bolting | 6.3 | 381 | 112 | 147 ($P < 0.001$) |

Discussion

When the heterozygous pollen parent was not sprayed, the back-crossed progeny segregated not significantly different from the expected 1:1 ratio. Following chlorsulfuron applications to the pollen parent, highly significant skewed segregation in favor of chlorsulfuron-resistant seedlings was observed. However, this effect was not as dramatic as spraying the ovule parent—see (b) above. Although herbicide applications inhibited the functions of herbicide-sensitive pollen, this establishes that pollen effects account for only a minor component of the skewed segregation.

Part (d). Plants heterozygous for the chlorsulfuron-resistant mutation (wtx30b) were either not sprayed, or sprayed with chlorsulfuron just prior to bolting. The back-crossed progeny ((wtx30b)x30b), resulting from pollen and non-sprayed homozygous 30b plants, were screened for chlorsulfuron resistance as described in Experiment 1.

Results

The results are given in Table 8 as follows:

TABLE 8

| Herbicide application (timing) | Number of seeds per pod | Number of herbicide-resistant seedlings | Number herbicide-sensitive seedlings |
| --- | --- | --- | --- |
| no spray | 6.4 | 223 | 0 |
| just prior to bolting | 3.4 | 111 | 0 |

Discussion

As expected, the back-crossed progeny did not segregate for chlorsulfuron resistance, since the pollen parent was homozygous for herbicide resistance and all developing embryos carry at least one allele for chlorsulfuron resistance. However, spraying the heterozygous female parent with chlorsulfuron resulted in a substantial reduction in seed set per pod. Since no embryo effects are expected, this experiment establishes that a major effect contributing to skewed segregation arises from the elimination of herbicide-sensitive ovules.

Experiment 6

Transgenic Alfalfa Plants (*Medicago sativa*)

A particular alfalfa line (P-1) is chosen for transformation and regeneration. Preferably, the P-1 line is an elite parental line from a commercially-successful alfalfa synthetic variety. Transformation is either accomplished via particle acceleration using immature cotyledons or somatic embryos derived from immature cotyledons (see, e.g., U.S. Pat. No. 5,324,646) or by Agrobacterium-mediated transformation (see, e.g., Wang et al., Hoffman et al., or Trieu et al., all supra). The gene construct used to transform P-1 includes the heterologous gene coding for EPSP synthase, which confers resistance to normally toxic levels of glyphosate (U.S. Pat. No. 5,554,798), operably linked to the heterologous gene for synthetic cryIC, which encodes a *Bacillus thuringiensis* delta-endotoxin conferring insect resistance. Regenerated plants are selected for their resistance to glyphosate (i.e., Roundup®) by spraying the plant with the herbicide one or more times during the life cycle of the plants. Seed is harvested from the self-pollinated, regenerated transgenic plants and/or multiple clones (i.e., cuttings) are established from the regenerated transgenic plants to create a transgenic glyphosate-resistant version of the P-1 line, designated P-1R. Theoretically, the P-1 and P-1R lines should only differ for the genes introduced via the transformation process (i.e., a single event).

The transgenic P-1R line is used as the pollen parent and crossed to plants of approximately 100 non-glyphosate resistant alfalfa lines. The seed resulting from these 100 cross combinations is bulked within a cross (ie., by parental combination or cross). Plants are grown from the seed of each of the 100 bulked crosses and tested for resistance to glyphosate by spraying the plants with the herbicide one or more times during the life cycle of the plants. The seed is harvested from the resistant plants and bulked within a cross to create 100 new glyphosate-resistant lines.

The 100 new glyphosate-resistant lines are randomly intermated (ie., crossed) to create polycross seed, designated as the first synthetic, or SYN-1. The SYN-1 seed is increased and maintained as breeder seed by planting seed of the polycross, spraying the plants with glyphosate one or more times during the life cycle of the plant, and harvesting the resultant seed.

Alternatively, the SYN-1 seed is used to produce foundation seed, registered seed or certified seed. Each time seed is produced on the SYN-1 plants it may be necessary to spray the plants with glyphosate one or more times during the life cycle of the plants to ensure that only resistant plants are included in the resultant bulked seed.

The P-1R alfalfa line, as well as any of the glyphosate-resistant lines resulting from the 100 original crosses with the P-1R line, can be used to introduce the transgene(s) into other alfalfa parental lines, using such well-known plant breeding processes as pedigree selection and back-crossing. Using the procedures set forth herein, P-1R and plants developed from P-1R can be intermated with other elite or non-elite alfalfa parental lines to produce additional polycross or synthetic varieties which will have the transgenes of interest.

To more clearly exemplify the advantages of the present invention, the following illustrations serve to demonstrate tetrasomic inheritance in alfalfa For the following examples, consider the transgene "A" to be dominant to the "wild type" allele "a".

| Type | Allelic constitution |
| --- | --- |
| Simplex | Aaaa |
| Duplex | AAaa |
| Nulliplex | aaaa |
| Triplex | AAAa |
| Tetraplex | AAAA |

Mating Type Example 1.
  Parents: Simplex (Aaaa)×Simplex (Aaaa).
  Gametes: 0/6=AA, 3/6=Aa, and 3/6=aa (both parents).
  Progeny: 1/4=AAaa, 1/2=Aaaa, and 1/4 aaaa.
  This is the same situation as that of disomic inheritance. Without spraying, segregation would be expected in a 3:1 ratio, with 75% of the progeny expressing the dominant transgene. In contrast, spraying the plants as set forth in the methods of this invention, would result in 100% of the progeny expressing the dominant transgene.
Mating Type Example 2.
  Parents: Duplex (AAaa) ×Duplex (AAaa).
  Gametes: 1/6=AA, 4/6=Aa, and 1/6=aa (both parents).
  Progeny: 1/36=AAAA, 8/36=AAAa, 18/36=AAaa, 8/36= Aaaa, and 1/36=aaaa.
  Without spraying, segregation would be expected in a 35:1 ratio, with 97% of the progeny expressing the dominant transgene. In contrast, spraying the plants as set forth in the methods of this invention, would result in 100% of the progeny expressing the dominant transgene.
Mating Type Example 3.
  Parents: Duplex (AAaa)×Simplex (Aaaa).
  Gametes: 1/6=AA, 4/6=Aa, and 1/6=aa (Duplex parent) and 0/6 AA, 3/6=Aa, and 3/6=aa (Simplex parent)
  Progeny: 1/12=AAAa, 5/12=AAaa, 5/12=Aaaa, and 1/12=aaaa.
  Without spraying, segregation would be expected in a 11:1 ratio, with 91.7% of the progeny expressing the dominant transgene. In contrast, spraying the plants as set forth in the methods of this invention, would result in 100% of the progeny expressing the dominant transgene.
Mating Type Example 4.
  Parents: Simplex (Aaaa)×Nulliplex (aaaa).
  Gametes: 0/6 AA, 3/6=Aa, and 3/6=aa (Simplex parent); 100% aa (Nulliplex parent).
  Progeny: 50% Aaaa and 50% aaaa.
  Without spraying, segregation would be expected in a 1:1 ratio, with 50% of the progeny expressing the dominant transgene. In contrast, spraying the plants as set forth in the methods of this invention, would result in 100% of the progeny expressing the dominant transgene.
Mating Type Example 5.
  Parents: Duplex (AAaa)×Nulliplex (aaaa).
  Gametes: 1/6 AA, 4/6=Aa, and 1/6=aa (Simplex parent); 100% aa (Nulliplex parent).
  Progeny: 1/6=AAu, 4/6=Aaaa, and 1/6 aaaa.
  Without spraying, segregation would be expected in a 5:1 ratio, with 83.3% of the progeny expressing the dominant transgene. In contrast, spraying the plants as set forth in the methods of this invention, would result in 100% of the progeny expressing the dominant transgene.

Any particular open pollinated or synthetic alfalfa population will most likely consist of plants which represent several, or all, of the different parental types being crossed in all possible combinations. Thus, introducing a transgene into such populations without the benefit of the present invention would result in less than 100% of the plants carrying the transgene(s) of interest.

Experiment 7

Transgenic Alfalfa Plants (*Medicago sativa*) using Backcrosses

The initial P-1R plants are produced according to the procedure set forth in Experiment 6.

Where the P-1 R plants differ from the P-1 plants for commercially important traits other than those trait(s) due to the transgene(s) alone, the P-1R plants can be backcrossed to the P-1 plants one or more times. Such differences between the P-1 and the initial P-1R plants could be due to several factors, including: 1) the inadvertent introduction of undesirable genes through the transformation process; or, 2) spontaneous mutations arising during the transformation, regeneration or growth of the P-1R plants. The likelihood that such genetic changes will require this backcrossing procedure is considered to be quite low.

The backcrossed seed is harvested, the plants grown from the harvested seed are tested for resistance to glyphosate by spraying the plants one or more during times during the life cycle of the plants, and the resistant plants are selected for selfing or further backcrossing. This process is terminated once transgenic P-1R plants are obtained which differ genotypically or phenotypically from the original P-1 plants only for the transgenes of interest (i.e., glyphosate and cryIC genes).

The transgenic, backcrossed P-1R line is then used as the pollen parent and crossed to plants of approximately 100 non-glyphosate resistant alfalfa lines. The SYN-1 is produced as set forth in Experiment 6.

Experiment 8

Alternative Method of Producing Alfalfa SYN-1

The transgenic P-1R line is produced as set forth in either Experiment 6 or Experiment 7.

Next, the P-1R line is used as the pollen parent and crossed to plants of approximately 100 non-glyphosate resistant alfalfa lines. The seed resulting from these 100 cross combinations is bulked. Bulking all of the seed at this stage will save at least one generation of growing time over the overall methods set forth in Experiments 6 and 7.

Plants are grown from the bulked seed, allowed to intermate, and sprayed with the herbicide one or more times during the life cycle of the plants. The seed is harvested from the resistant plants and bulked to create the first synthetic, or SYN-1.

The SYN-1 seed is increased and maintained as breeder seed by planting seed of the polycross, spraying the plants with glyphosate one or more times during the life cycle of the plant, and harvesting the resultant seed.

Alternatively, the SYN-1 seed is used to produce foundation seed, registered seed or certified seed. Each time seed is produced on the SYN-1 plants it may be necessary to spray the plants with glyphosate to ensure that only resistant plants are included in the resultant bulked seed.

The P-1R alfalfa line, as well as any of the glyphosate-resistant lines within the SYN-1 population, can be used to introduce the transgene(s) into other alfalfa parental lines, using such well-known plant breeding processes as pedigree selection and back-crossing. Using the procedures set forth herein, P-1R and plants developed from P-1R can be intermated with other elite or non-elite alfalfa parental lines to produce additional polycross or synthetic varieties which will have the transgenes of interest.

Experiment 9

Transgenic Red Clover Plants (*Trifolium pratense*)

The methods of Experiments 6, 7 or 8 are repeated using the Agrobacterium-mediated transformation of parental red clover plants (Quesbenberry et al., supra). This time, the construct contains the GUS gene coding for Basta® herbicide resistance (Khan et al., supra) operably linked to the cryIA gene from Bt coding for resistance to polyphagous insect pests (Voisey et al., supra). Using the procedures set forth in Experiments 6, 7 or 8, clover populations are created which contain the transgenes of interest.

Overall Summary of the Experimental Results

The experimental results given above clearly establish that applying a phytotoxin to plants carrying a phytotoxin-resistance transgene prevents the development of phytotoxin-sensitive progeny. The important consequence of this is the true breeding nature of phytotoxin resistance from heterozygous plants; that is, phytotoxin applications can be used to induce a skewed segregation by selective abortion of phytotoxin-sensitive progeny. The theoretical mechanism by which this happens is believed to be that the phytotoxin is taken up by the phytotoxin-resistant plant, having no effect on the plant itself due to the phytotoxin-resistant gene it contains. However, following meiosis, pollination, and fertilization some phytotoxin-sensitive cells are expected to develop on plants heterozygous for alleles conferring phytotoxin resistance. These cells develop as consequence of allele segregation, and will involve pollen, ovules and embryos. For plants heterozygous for a single dominant allele conferring phytotoxin resistance, this is expected to be half the pollen cells, half the egg cells in ovules, and a quarter of the embryos. The application of the phytotoxin to plants heterozygous for alleles conferring phytotoxin resistance will effectively kill these phytotoxin-sensitive cells, resulting in the transmission of only phytotoxin-resistant progeny.

The results of Experiment 5 in particular show that this is what is in fact happening. The skewed segregation induced by applications of phytotoxin to plants heterozygous for phytotoxin resistance, results from the cumulative effects of the phytotoxin on pollen, ovules and embryos that do not carry a resistance allele. The primary effect is on the selective inhibition of phytotoxin sensitive ovules or abortion of embryos, with a partial effect also derived from the selective inhibition of phytotoxin-sensitive pollen.

Experiments 6, 7, 8 and 9 demonstrate the utility of the present invention for the production of open pollinated or synthetic varieties of alfalfa and clover, wherein such populations maintain one or more transgenes of interest at levels higher than could be obtained using conventional plant husbandry and plant breeding methods.

Industrial Application

This invention has a number of applications in the seed industry. The main applications in the seed industry will involve transgenic plants in which resistance to phytotoxin is use as a selectable marker for transferring other useful genes to the same locus via genetic engineering approaches.

Applications to the seed industry will involve all open pollinated crops where seed is produced from heterozygous plants. These mainly involve forage crops (e.g., forage brassicas, forage legumes such as alfalfa, clover, grasses), forestry, and some vegetable (e.g., asparagus) and ornamental flower crops.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for biasing a crop plant which is heterozygous for a transgene coding for a protein that confers resistance to a translocatable herbicide towards the production of seeds which carry the transgene, comprising contacting the crop plant containing a gene construct comprising the transgene with the translocatable herbicide at two or more stages of commercial seed production, wherein the crop plant is part of an open-pollinated population or a synthetic variety and wherein a higher proportion of seed of the crop plant comprise the transgene as compared to seed of a plant that is not contacted with the herbicide.

2. The method of claim 1 wherein the two or more stages of commercial seed production are selected from the group consisting of breeder seed production stage, foundation seed production stage, registered seed production stage and certified seed production stage.

3. The method of claim 1 wherein the contacting is once during each of the two or more stages of commercial seed production.

4. The method of claim 1 wherein the contacting is one or more times during each of the two or more stages of commercial seed production.

5. The method of claim 1 further comprising confirming the presence of the transgene at one or more of stages of commercial production.

6. A method for increasing the presence of a transgene that codes for a protein that confers resistance to a translocatable herbicide in commercial seed of a synthetic or an open pollinated population comprising:
    a) introducing one or more plants heterozygous for a transgene coding for a protein that confers resistance to a translocatable herbicide into a synthetic or open pollinated population;
    b) contacting the synthetic or open pollinated population produced in step a) with the translocatable herbicide at two or more stages of commercial seed production; and
    c) bulking the seed produced in step b) to produce commercial seed wherein a higher proportion of seed comprise the transgene as compared to seed of the synthetic or open pollinated population that is not contacted with the herbicide.

7. A method for biasing a crop plant which is heterozygous for a transgene coding for a protein that confers resistance to a translocatable herbicide towards the production of seeds which carry the transgene comprising contacting the crop plant containing a gene construct comprising the transgene with the translocatable herbicide more than once during the life of the crop plant, wherein the crop plant is part of an open-pollinated population or a synthetic variety and wherein a higher proportion of seed of the crop plant comprise the transgene as compared to seed of a plant that is not contacted with the herbicide.

8. A method of selectively inhibiting herbicide-sensitive plant ovules, embryos and/or pollen in order to bias a crop plant which is heterozygous for a transgene coding for a protein that confers resistance to a translocatable herbicide towards the production of seeds which carry the transgene comprising contacting the crop plant containing a gene construct comprising the transgene with the translocatable herbicide more than once during the life of the crop plant, wherein the crop plant is part of an open-pollinated population or a synthetic variety and wherein said contacting results in selective inhibition of herbicide sensitive plant ovules, embryos, and/or pollen, and a consequent higher proportion of seed comprise the transgene as compared to seed of the synthetic or open pollinated population that is not contacted with the herbicide.

9. A method of selectively inhibiting herbicide-sensitive plant ovules in order to bias a crop plant which is heterozygous for a transgene coding for a protein that confers resistance to a translocatable herbicide towards the production of seeds which carry the transgene comprising contacting the crop plant containing a gene construct comprising the transgene with the translocatable herbicide more than once during the life of the crop plant, wherein the crop plant is part of an open-pollinated population or a synthetic variety and wherein said contacting results in selective inhibition of herbicide-sensitive plant ovules and a consequent higher proportion of seed of the crop plant comprise the transgene as compared to seed of a plant that is not contacted with the herbicide.

10. A method of selectively aborting herbicide-sensitive plant embryos in order to bias a crop plant which is heterozygous for a transgene coding for a protein that confers resistance to a translocatable herbicide towards the production of seeds which carry the transgene comprising contacting the crop plant containing a gene construct comprising the transgene with the translocatable herbicide more than once during the life of the crop plant, wherein the crop plant is part of an open-pollinated population or a synthetic variety and wherein said contacting results in selective abortion of herbicide-sensitive plant embryos and a consequent higher proportion of seed of the crop plant comprise the transgene as compared to seed of a plant that is not contacted with the herbicide.

11. A method of selectively inhibiting herbicide-sensitive pollen in order to bias a crop plant which is heterozygous for a transgene coding for a protein that confers resistance to a translocatable herbicide towards the production of seeds which carry the transgene comprising contacting the crop plant containing a gene construct comprising the transgene with the translocatable herbicide more than once during the life of the crop plant, wherein the crop plant is part of an open-pollinated population or a synthetic variety and wherein said contacting results in selective inhibition of herbicide-sensitive pollen and a consequent higher proportion of seed of the crop plant comprise the transgene as compared to seed of a implant that is not contacted with the herbicide.

12. The method of claim 7 wherein the contacting is during the vegetative or reproductive growth phase of the crop plant.

13. The method of claim 7 wherein the crop plant is alfalfa or clover.

14. The method of claim 7 wherein the gene construct further comprises one or more additional transgene(s), such that the crop plant is biased towards the production of seeds which carry all of the transgenes.

15. The method of claim 7 wherein the herbicide is chlorsulfuron.

16. The method of claim 7 wherein the crop plant is a forage crop plant, a tree, a vegetable crop plant or an ornamental flowering plant.

17. The method as claimed in claim 16 wherein the forage crop plant is a forage brassica plant, a forage legume plant, or a grass plant.

18. The method of claim 7 which further comprises, prior to the contacting, the step of introducing the gene construct into the crop plant or into the seed from which the crop plant is grown.

19. The method as claimed in claim 17 wherein the gene construct is located in the genome of the crop plant at an integration site immediately adjacent to a desirable homologous gene, such that when the crop plant is contacted with said translocatable herbicide the crop plant is biased towards the production of seeds which carry both the transgene and the homologous gene.

20. The method of claim 7 wherein the open-pollinated population or synthetic variety comprises a mixture of two or more different crop plants.

21. The method of claim 20 wherein each of the two or more different crop plants are selected from the group consisting of forage brassica plants, forage legume plants and grass plants.

22. A method of producing a new synthetic alfalfa variety comprising the step of:
   1) producing a transgenic alfalfa plant, wherein the transgenic alfalfa plant is heterozygous for an introduced gene construct which comprises a heterologous gene coding for a protein that confers translocatable herbicide resistance operably linked to a heterologous gene of interest;
   2) using the transgenic alfalfa plant produced by step 1) as a parent and crossing the transgenic alfalfa plant to one or more alfalfa plants which do not contain the translocatable herbicide resistance gene operably linked to the heterologous gene of interest;
   3) applying the translocatable herbicide more than once during the life cycle of the plants in step 2); and
   4) harvesting and bulking the resultant seed to produce a new synthetic alfalfa variety wherein a higher proportion of seed of the new synthetic alfalfa variety contain the translocatable herbicide resistance gene operably linked to the gene of interest as compared to seed of plants that are not contacted with the herbicide.

23. The method of claim 22 further comprising the following steps:
   5) growing and intermating plants from the bulked seed obtained in step 4);
   6) applying the translocatable herbicide one or more times during the life cycle of the plant in step 5); and,
   7) harvesting and bulking the resultant seed, wherein a higher proportion of said seed contain the translocatable herbicide resistance gene operably linked to the gene of interest as compared to seed of plants that are not contacted with the herbicide.

24. The method of claim 22 wherein the heterologous gene of interest codes for a product that confers herbicide resistance, insect resistance, decreased lignin content or reduced leaf senescence.

* * * * *